(12) United States Patent
Löffler et al.

(10) Patent No.: US 7,566,763 B2
(45) Date of Patent: *Jul. 28, 2009

(54) STABLE DISPERSION CONCENTRATES

(75) Inventors: Matthias Löffler, Niedernhausen (DE); Roman Morschhäuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 413 days.

This patent is subject to a terminal disclaimer.

(21) Appl. No.: 10/394,787

(22) Filed: Mar. 21, 2003

(65) Prior Publication Data

US 2003/0232028 A1    Dec. 18, 2003

(30) Foreign Application Priority Data

Mar. 23, 2002    (DE) ............................... 102 13 142

(51) Int. Cl.
*C08F 12/30* (2006.01)
*A61K 8/02* (2006.01)

(52) U.S. Cl. .................... 526/287; 526/250; 514/772.4; 514/937; 424/401

(58) Field of Classification Search ................ 424/401, 424/70.1, 70.5, 59, 61; 526/287, 250; 514/772.4, 514/937

See application file for complete search history.

(56) References Cited

U.S. PATENT DOCUMENTS

| | | | | |
|---|---|---|---|---|
| 4,610,311 A * | 9/1986 | Bronner et al. | ............... | 169/45 |
| 5,104,645 A | 4/1992 | Cardin et al. | ................. | 424/70 |
| 5,275,809 A | 1/1994 | Chen et al. | | |
| 5,296,218 A | 3/1994 | Chen et al. | | |
| 5,879,718 A | 3/1999 | Sebillote-Arnaud | ......... | 424/705 |
| 6,107,500 A | 8/2000 | Prossel et al. | ............... | 554/169 |
| 6,120,780 A | 9/2000 | Dupuis et al. | ............... | 424/401 |
| 6,403,074 B1 | 6/2002 | Blankenburg et al. | .... | 424/70.12 |
| 6,468,549 B1 | 10/2002 | Dupuis et al. | ............... | 424/401 |
| 6,645,476 B1 | 11/2003 | Loeffler et al. | | |
| 6,833,419 B2 * | 12/2004 | Morschhauser et al. | ..... | 526/288 |
| 6,891,011 B2 * | 5/2005 | Morschhauser et al. | ..... | 526/288 |
| 7,022,791 B2 * | 4/2006 | Loffler et al. | ............... | 526/288 |
| 7,025,973 B2 | 4/2006 | Loeffler et al. | | |
| 7,053,146 B2 * | 5/2006 | Morschhauser et al. | ..... | 524/461 |
| 7,081,507 B2 * | 7/2006 | Morschhauser et al. | ..... | 526/288 |
| 7,186,405 B2 | 3/2007 | Loeffler et al. | | |
| 2003/0031643 A1 | 2/2003 | L'Alloret et al. | | |

FOREIGN PATENT DOCUMENTS

| | | |
|---|---|---|
| CA | 236 3079 | 8/2000 |
| DE | 197 27 950 | 1/1999 |
| DE | 199 07 587 | 8/2000 |
| DE | 199 51 877 | 5/2001 |
| EP | 0 815 828 | 1/1998 |
| EP | 0 815 844 | 1/1998 |
| EP | 0815 845 | 1/1998 |
| JP | 2001-295994 | 7/2002 |
| JP | 2001-296935 | 7/2002 |
| JP | 2003-012444 | 1/2003 |
| WO | WO 99/04750 | 2/1999 |
| WO | WO 02/44231 | 6/2002 |

OTHER PUBLICATIONS

English abstract for WO 02/44231, Jun. 6, 2002.
English abstract for DE 19907587, Aug, 24, 2000.
English abstract for DE 19951877, May 3, 2001.

* cited by examiner

*Primary Examiner*—Gina C Yu
(74) *Attorney, Agent, or Firm*—Richard P. Silverman; Tod A. Waldrop

(57) ABSTRACT

The invention provides dispersion concentrates comprising at least one polymer obtainable by free-radical copolymerization of A) acryloyldimethyltauric acid and/or acryloyldimethyltaurates,
B) optionally one or more further olefinically unsaturated, noncationic comonomers,
C) optionally one or more olefinically unsaturated, cationic comonomers,
D) optionally one or more silicon-containing component(s),
E) optionally one or more fluorine-containing component(s),
F) optionally one or more macromonomers,
G) where the copolymerization optionally takes place in the presence of at least one polymeric additive, with the proviso that the component A) is copolymerized with at least one component chosen from the group D) to G).

16 Claims, No Drawings

STABLE DISPERSION CONCENTRATES

The present invention relates to dispersion concentrates comprising copolymers based on acryloyldimethyltauric acid or salts thereof (AMPS), obtainable by copolymerization of AMPS with one or more olefinic comonomer(s) and components with functional groups.

The application PCT/EP 01/13860 describes a new class of polymers based on acryloyldimethyltauric acid or salts thereof. These polymers confer broad performance properties and can be used as thickener, bodying agent, emulsifier, dispersant, lubricant, conditioner and/or stabilizer in cosmetic, dermatological and pharmaceutical compositions.

The copolymers based on AMPS, prepared preferably by precipitation polymerization, in accordance with the prior art are pulverulent substances with performance disadvantages resulting therefrom. In addition to a risk of dust explosion, the dust can harbor dangers in cases of inhalation, and also the storage stability of the powders is impaired by hygroscopicity.

When processing or using the pulverulent products, the dissolution operation (the polymers are preferably incorporated into aqueous media) is in most cases very time-consuming. The dissolution operation of the pulverulent products can, depending on the size of the batch, take one hour and more. In addition, incomplete dissolution/swelling of the pulverulent products is often observed, which leads to a reduction in the quality and stability of the end formulation (formation of lumps). In addition, the processing and/or use of the pulverulent products generally requires specific stirring and dispersion devices in order to dissolve, or suspend, the AMPS polymers in the compositions.

The object was to find liquid forms of the pulverulent polymers based on acryloyldimethyltauric acid or salts thereof, preferably prepared by precipitation polymerization (AMPS). Preference is given here to dispersions of the polymers in a liquid matrix comprising oil, emulsifier, dispersant and/or water. Preference is given here to liquid-disperse forms with the highest possible polymer proportion, low viscosity coupled with high stability of the dispersion. The oil and emulsifier/dispersant proportions used are preferably cosmetically and pharmaceutically acceptable raw materials.

Surprisingly, it has been found that AMPS copolymers are suitable in an excellenrt manner for the preparation of dispersion concentrates.

The invention provides dispersion concentrates comprising

I) 5 to 80% by weight, preferably 20 to 60% by weight, particularly preferably 30 to 40% by weight, of a copolymer obtainable by free-radical copolymerization of
A) acryloyldimethyltauric acid and/or acryloyldimethyltaurates,
B) optionally one or more further olefinically unsaturated, non-cationic, optionally crosslinking comonomers which have at least one oxygen, nitrogen, sulfur or phosphorus atom and have a molecular weight of less than 500 g/mol,
C) optionally one or more olefinically unsaturated, cationic comonomers which have at least one oxygen, nitrogen, sulfur or phosphorus atom and have a molecular weight of less than 500 g/mol,
D) optionally one or more at least monofunctional silicon-containing component(s) capable of free-radical polymerization,
E) optionally one or more at least monofunctional fluorine-containing component(s) capable of free-radical polymerization,
F) optionally one or more mono- or polyolefinically unsaturated, optionally crosslinking macromonomers which have at least one oxygen, nitrogen, sulfur or phosphorus atom and have a number-average molecular weight of greater than or equal to 200 g/mol, where the macromonomers are not a silicon-containing component D) or fluorine-containing component E),
G) where the copolymerization optionally takes place in the presence of at least one polymeric additive with number-average molecular weights of from 200 g/mol to $10^9$ g/mol,
H) with the proviso that the component A) is copolymerized with at least one component chosen from one of groups D) to G),
II) 20 to 95% by weight, preferably 30 to 80% by weight, particularly preferably 40 to 60% by weight, of one or more emulsifiers and/or an oil phase and
III) 0 to 30% by weight, preferably 0 to 10% by weight, particularly preferably 0 to 5% by weight, of water.

The copolymers according to component I) preferably have a molecular weight of from $10^3$ to $10^9$ g/mol, particularly preferably from $10^4$ to $10^7$ g/mol, particularly preferably $5*10^4$ to $5*10^6$ g/mol.

The acryloyldimethyltaurates may be the inorganic or organic salts of acryloyldimethyltauric acid (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Preference is likewise given to the monoalkylammonium, dialkylammonium, trialkylammonium and/or tetraalkylammonium salts, where the alkyl substituents of the amines may be, independently of one another, $(C_1-C_{22})$-alkyl radicals or $(C_2-C_{10})$-hydroxyalkyl radicals. In addition, preference is also given to mono- to triethoxylated ammonium compounds with varying degrees of ethoxylation. It should be noted that mixtures of two or more of the abovementioned representatives are also within the meaning of the invention. The degree of neutralization of the acryloyldimethyltauric acid can be between 0 and 100%, particular preference being given to a degree of neutralization of more than 80%.

Based on the total mass of the copolymers, the content of acryloyldimethyltauric acid or acryloyldimethyltaurates is at least 0.1% by weight, preferably 20 to 99.5% by weight, particularly preferably 50 to 98% by weight.

Comonomers B) which can be used are all olefinically unsaturated, non-cationic monomers whose reaction parameters permit a copolymerization with acryloyldimethyltauric acid and/or acryloyldimethyltaurates in the respective reaction media.

As comonomers B), preference is given to unsaturated carboxylic acids and anhydrides and salts thereof, and also esters thereof with aliphatic, olefinic, cycloaliphatic, arylaliphatic or aromatic alcohols having a carbon number from 1 to 30.

As unsaturated carboxylic acids, particular preference is given to acrylic acid, methacrylic acid, styrenesulfonic acid, maleic acid, fumaric acid, crotonic acid, itaconic acid and senecioic acid.

As counterions, preference is given to $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, where the alkyl substituents of the amines may, independently of one another, be $(C_1-C_{22})$-alkyl radicals or $(C_2-C_{10})$-hydroxyalkyl radicals. In addition, it is also possible to use mono- to triethoxylated ammonium compounds with varying degrees of ethoxylation. The degree of neutralization of the carboxylic acids can be between 0 and 100%.

As comonomers B), preference is also given to open-chain N-vinylamides, preferably N-vinylformamide (VIFA), N-vinylmethylformamide, N-vinylmethylacetamide (VIMA) and N-vinylacetamide; cyclic N-vinylamides (N-vinyllactams) with a ring size from 3 to 9, preferably N-vinylpyrrolidone (NVP) and N-vinylcaprolactam; amides of acrylic acid and methacrylic acid, preferably acrylamide, methacrylamide, N,N-dimethylacrylamide, N,N-diethylacrylamide and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide and 2-(methacryloyloxy)ethyl monosuccinate; N,N-dimethylaminomethacrylate; diethylaminomethyl methacrylate; acryl- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable as comonomers B) are inorganic acids and salts and esters thereof. Preferred acids are vinylphosphonic acid, vinylsulfonic acid, allylphosphonic acid and methallylsulfonic acid.

The proportion by weight of the comonomers B), based on the total mass of the copolymers, can be 0 to 99.8% by weight and is preferably 0.5 to 80% by weight, particularly preferably 2 to 50% by weight.

Suitable comonomers C) are all olefinically unsaturated monomers with a cationic charge which are able to form copolymers in the chosen reaction media with acryloyldimethyltauric acid or salts thereof. The resulting distribution of the cationic charges over the chains may be random, alternating, block-like or gradient-like. It may be noted that the cationic comonomers C) also include those which carry the cationic charge in the form of a betainic, zwitterionic or amphoteric structure.

Comonomers C) for the purposes of the invention are also amino-functionalized precursors which can be converted by polymer-analogous reactions into their corresponding quaternary derivatives (e.g. reaction with dimethyl sulfate, methyl chloride), zwitterionic derivatives (e.g. reaction with hydrogen peroxide), betainic derivatives (e.g. reaction with chloroacetic acid), or amphomeric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride
N-methyl-4-vinylpyridinium chloride
dimethylaminoethyl methacrylate,
dimethylaminopropyl methacrylamide,
methacryloylethyl N-oxide and/or
methacryloylethylbetaine.

The proportion by weight of the comonomers C) can, based on the total mass of the copolymers, be 0.1 to 99.8% by weight, preferably 0.5 to 30% by weight and particularly preferably 1 to 20% by weight.

Suitable silicon-containing components D) capable of polymerization are all at least monoolefinically unsaturated compounds which, under the reaction conditions chosen in each case, are capable of free-radical copolymerization. In this connection, the distribution of the individual silicon-containing monomers over the resulting polymer chains does not necessarily have to be random. The formation of, for example, block-like (including multiblock-like) or gradient-like structures is also within the meaning of the invention. Combinations of two or more different silicon-containing representatives are also possible. The use of silicon-containing components having two or more polymerization-active groups leads to the formation of branched or crosslinked structures.

Preferred silicon-containing components are those according to formula (I).

Here, $R^1$ is a function capable of polymerization from the group of vinylically unsaturated compounds which is suitable for building up polymeric structures by free-radical routes. Preferably, $R^1$ is a vinyl, allyl, methallyl, methylvinyl, acrylic ($CH_2$=CH—CO—), methacrylic ($CH_2$=C[$CH_3$]—CO—), crotonyl, senecionyl, itaconyl, maleinyl, fumaryl or styryl radical.

To join the silicon-containing polymer chain to the reactive end group $R^1$, a suitable chemical bridge Z is required. Preferred bridges Z are —O—, —(($C_1$-$C_{50}$)alkylene)-, —(($C_6$-$C_{30}$)arylene)- , —(($C_5$-$C_8$)cycloalkylene)—, —(($C_1$-$C_{50}$) alkenylene)- , (polypropylene oxide) $_n$- , -(polyethylene oxide)$_o$- , -(polypropylene oxide)$_n$(polyethylene oxide)$_o$- , where n and o, independently of one another, are numbers from 0 to 200 and the distribution of the EO/PO units may be random or block-like. Also suitable as bridging groups Z are —(($C_1$-$C_{10}$)alkyl)-(Si($OCH_3$)$_2$)- and —(Si($OCH_3$)$_2$)-.

The polymeric middle section is represented by silicon-containing repeat units.

The radicals $R^3$, $R^4$, $R^5$ and $R^6$ are, independently of one another, —$CH_3$, —O—$CH_3$, —$C_6H_5$ or —O—$C_6H_5$. The indices w and x represent stoichiometric coefficients which, independently of one another, are 0 to 500, preferably 10 to 250.

The distribution of the repeat units over the chain can be not only purely random, but also block-like, alternating or gradient-like.

$R^2$ can on the one hand symbolize an aliphatic, olefinic, cycloaliphatic, arylaliphatic or aromatic ($C_1$-$C_{50}$)-hydrocarbon radical (linear or branched) or —OH, —$NH_2$, —N($CH_3$)$_2$, —$R^7$ or be the structural unit [-Z-$R^1$]. The meaning of the two variables Z and $R^1$ has already been explained. $R^7$ is a further Si-containing group. Preferred $R^7$ radicals are —O—Si($CH_3$)$_3$, —O—Si(Ph)$_3$, —O—Si(O—Si($CH_3$)$_3$)$_2$$CH_3$) and —O—Si(O—Si(Ph)$_3$)$_2$Ph).

If $R^2$ is an element of group [—Z—$R^1$], the monomers are difunctional and can be used for the crosslinking of the resulting polymer structures.

Formula (I) describes not only vinylically functionalized, silicon-containing polymer species with a polymer-typical distribution, but also defined compounds with discreet molecular weights.

Particularly preferred silicon-containing components are the following acrylically or methacrylically modified silicon-containing components:

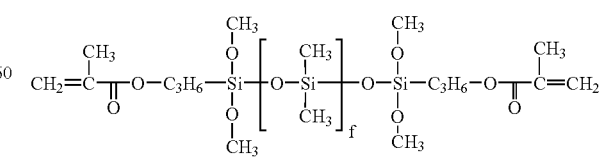

methacryloxypropyldimethylsilyl end-blocked polydimethylsiloxanes (f=2 to 500)

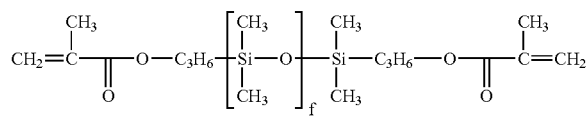

methacryloxypropyl end-blocked polydimethylsiloxanes (f=2 to 500)

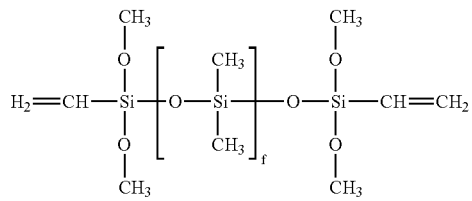

vinyldimethoxysilyl end-blocked polydimethylsiloxanes (f=2 to 500)

Based on the total mass of the copolymers, the content of silicon-containing components can be up to 99.9% by weight, preferably 0.5 to 30% by weight, particularly preferably 1 to 20% by weight.

Suitable fluorine-containing components E) which are capable of polymerization are all at least monoolefinically unsaturated compounds which are capable of free-radical copolymerization under the reaction conditions chosen in each case. In this connection, the distribution of the individual fluorine-containing monomers over the resulting polymer chains does not necessarily have to be random. The formation of, for example, block-like (including multiblock-like) or gradient-like structures is also within the meaning of the invention. Combinations of two or more different, fluorine-containing components E) is also possible, in which case it is clear to the expert that monofunctional representatives lead to the formation of comb-like structures, whereas di-, tri-, or polyfunctional components E) lead to at least partially crosslinked structures.

Preferred fluorine-containing components E) are those according to formula (II).

$$R^1—Y—C_rH_{2r}C_sF_{2s}CF_3 \quad (II)$$

Here, $R^1$ is a function capable of polymerization from the group of vinylically unsaturated compounds which is suitable for building up polymeric structures by free-radical routes. Preferably, $R^1$ is a vinyl, allyl, methallyl, methylvinyl, acrylic ($CH_2$=CH—CO—), methacrylic ($CH_2$=C[$CH_3$]—CO—), crotonyl, senecionyl, itaconyl, maleinyl, fumaryl or styryl radical, particularly preferably an acrylic and methacrylic radical.

To join the fluorine-containing group to the reactive end group $R^1$, a suitable chemical bridge Y is required. Suitable bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$-$C_{50}$)alkyl—O—, —O—phenyl—O—, —O—benzyl—O—, —O—($C_5$-$C_8$)cycloalkyl—O—, —O—($C_1$-$C_{50}$) alkenyl—O—, —O—(CH($CH_3$)—$CH_2$—O)$_n$—, —O—($CH_2$—$CH_2$—O)$_n$— and —O—([CH—$CH_2$—O]$_n$—[$CH_2$—$CH_2$—O]$_m$)$_o$—, where n, m and o, independently of one another, are numbers from 0 to 200 and the distribution of the EO and PO units may be random or block-like.

r and s are stoichiometric coefficients which, independently of one another, are numbers from 0 to 200.

Preferred fluorine-containing components E) according to formula (II) are
perfluorohexylethanol methacrylate,
perfluorohexylpropanol methacrylate,
perfluorooctylethanol methacrylate,
perfluorooctylpropanol methacrylate,
perfluorohexylethanolyl polyglycol ether methacrylate,
perfluorohexoylpropanoyl poly[ethyl glycol-co-propylene glycol ether] acrylate, perfluorooctylethanolyl poly[ethyl glycol block co-propylene glycol ether] methacrylate,
perfluorooctylpropanoyl polypropylene glycol ether methacrylate.

Based on the total mass of the copolymer, the content of fluorine-containing components can be up to 99.9% by weight, preferably 0.5 to 30% by weight, particularly preferably 1 to 20% by weight.

The macromonomers F) are at least monoolefinically functionalized polymers with one or more discrete repeat units and a number-average molecular weight of greater than or equal to 200 g/mol. For the copolymerization, it is also possible to use mixtures of chemically different macromonomers F). The macromonomers are polymeric structures which are formed from one or more repeat unit(s) and have a molecular weight distribution characteristic of polymers.

Preferred macromonomers F) are compounds according to formula (III).

$$R^1—Y—[(A)_v—(B)_w—(C)_x-(D)_z]—R^2 \quad (III)$$

$R^1$ is a function capable of polymerization from the group of vinylically unsaturated compounds which are suitable for building up polymeric structures by free-radical routes. Preferably, $R^1$ is a vinyl, allyl, methallyl, methylvinyl, acrylic ($CH_2$=CH—CO—), methacrylic ($CH_2$=C[$CH_3$]—CO—), crotonyl, senecionyl, itaconyl, maleinyl, fumaryl or styryl radical.

To join the polymer chain to the reactive end group, a suitable bridging group Y is required. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—,
—NH— and —N($CH_3$)—, particularly preferably —O—.

The polymeric middle section of the macromonomers is represented by the discrete repeat units A, B, C and D. Preferred repeat units A, B, C and D are derived from acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide and diisopropylacrylamide.

The indices v, w, x and z in formula (III) represent the stoichiometric coefficients relating to the repeat units A, B, C and D. v, w, x, and z are, independently of one another, 0 to 500, preferably 1 to 30, while the sum of the four coefficients must on average be $\geq 1$.

The distribution of the repeat units over the macromonomer chain can be random, block-like, alternating or gradient-like.

$R^2$ is a linear or branched aliphatic, olefinic, cycloaliphatic, arylaliphatic or aromatic ($C_1$-$C_{50}$)-hydrocarbon radical, OH, —$NH_2$, —N($CH_3$)$_2$ or is identical to the structural unit [—Y—$R^1$].

If $R^2$ is [—Y—$R^1$], the macromonomers are difunctional and are suitable for the crosslinking of the copolymers.

Particularly preferred macromonomers F) are acrylically or methacrylically monofunctionalized alkyl ethoxylates according to the formula (IV).

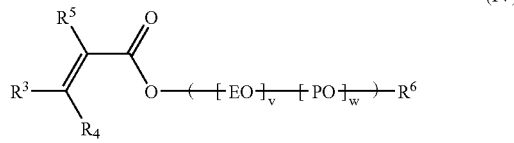

$R_3$, $R_4$, $R_5$ and $R_6$ are, independently of one another, hydrogen or n-aliphatic, isoaliphatic, olefinic, cycloaliphatic, arylaliphatic or aromatic ($C_1$-$C_{30}$)-hydrocarbon radicals.

Preferably, $R_3$ and $R_4$ are H or —$CH_3$, particularly preferably H; $R_5$ is H or —$CH_3$; and $R_6$ is an n-aliphatic, isoaliphatic, olefinic, cycloaliphatic, arylaliphatic or aromatic ($C_1$-$C_{30}$)-hydrocarbon radical.

v and w are in turn the stoichiometric coefficients relating to the ethylene oxide units (EO) and propylene oxide units (PO). v and w are, independently of one another, 0 to 500, preferably 1 to 30, where the sum of v and w must on average be $\geq 1$. The distribution of the EO and PO units over the macromonomer chain may be random, block-like, alternating or gradient-like.

In addition, particularly preferred macromonomers F) have the following structure according to formula (IV):

|  | $R^3$ | $R^4$ | $R^5$ | $R^6$ | v | w |
|---|---|---|---|---|---|---|
| Genapol ® LA-030 methacrylate | H | H | —$CH_3$ | -lauryl | 3 | 0 |
| Genapol ® LA-070 methacrylate | H | H | —$CH_3$ | -lauryl | 7 | 0 |
| Genapol ® LA-200 methacrylate | H | H | —$CH_3$ | -lauryl | 20 | 0 |
| Genapol ® LA-250 methacrylate | H | H | —$CH_3$ | -lauryl | 25 | 0 |
| Genapol ® T-080 methacrylate | H | H | —$CH_3$ | -talc | 8 | 0 |
| Genapol ® T-080 acrylatetalc | H | H | H | -Talk | 8 | 0 |
| Genapol ® T-250 methacrylate | H | H | —$CH_3$ | -talc | 25 | 0 |
| Genapol ® T-250 crotonate | —$CH_3$ | H | —$CH_3$ | -talc | 25 | 0 |
| Genapol ® OC-030 methacrylate | H | H | —$CH_3$ | -octyl | 3 | 0 |
| Genapol ® OC-105 methacrylate | H | H | —$CH_3$ | -octyl | 10 | 5 |
| Genapol ® Behenyl-010-metharyl | H | H | H | -behenyl | 10 | 0 |
| Genapol ® Behenyl-020-metharyl | H | H | H | -behenyl | 20 | 0 |
| Genapol ® Behenyl-010-senecionyl | —$CH_3$ | —$CH_3$ | H | -behenyl | 10 | 0 |
| Genapol ® PEG-440 diacrylate | H | H | H | -acryl | 10 | 0 |
| Genapol ® B-11-50 methacrylate | H | H | —$CH_3$ | -butyl | 17 | 13 |
| Genapol ® MPEG-750 methacrylate | H | H | —$CH_3$ | -methyl | 18 | 0 |
| Genapol ® P-010 acrylate | H | H | H | -phenyl | 10 | 0 |
| Genapol ® O-050 acrylate | H | H | H | -oleyl | 5 | 0 |

Also particularly suitable as macromonomers F) are esters of (meth)acrylic acid with ($C_{10}$-$C_{18}$)-fatty alcohol polyglycol ethers with 8 EO units (Genapol® C-080)

$C_{11}$-oxo alcohol polyglycol ethers with 8 EO units (Genapol® UD-080)

($C_{12}$-$C_{14}$)-fatty alcohol polyglycol ethers with 7 EO units (Genapol® LA-070)

($C_{12}$-$C_{14}$)-fatty alcohol polyglycol ethers with 11 EO units (Genapol® LA-110)

($C_{16}$-$C_{18}$)-fatty alcohol polyglycol ethers with 8 EO units (Genapol® T-080)

($C_{16}$-$C_{18}$)-fatty alcohol polyglycol ethers with 15 EO units (Genapol® T-150)

($C_{16}$-$C_{18}$)-fatty alcohol polyglycol ethers with 11 EO units (Genapol® T-110)

($C_{16}$-$C_{18}$)-fatty alcohol polyglycol ethers with 20 EO units (Genapol® T-200)

($C_{16}$-$C_{18}$)-fatty alcohol polyglycol ethers with 25 EO units (Genapol® T-250)

($C_{18}$-$C_{22}$)-fatty alcohol polyglycol ethers with 25 EO units and/or iso-($C_{16}$-$C_{18}$)-fatty alcohol polyglycol ethers with 25 EO units The Genapol® grades are products from Clariant, GmbH.

Preferably, the molecular weight of the macromonomers F) is 200 g/mol to $10^6$ g/mol, particularly preferably 150 to $10^4$ g/mol and particularly preferably 200 to 5000 g/mol.

Based on the total mass of the copolymers, suitable macromonomers can be used up to 99.9% by weight. Preferably, the ranges 0.5 to 30% by weight and 70 to 99.5% by weight are used. Particular preference is given to proportions of from 1 to 20% by weight and 75 to 95% by weight.

Preferred copolymers are those obtainable by copolymerization of at least components A), C) and D).

Further preferred copolymers are those obtainable by copolymerization of at least components A), C) and E).

Further preferred copolymers are those obtainable by copolymerization of at least components A), D) and F).

Further preferred copolymers are those obtainable by copolymerization of at least components A) and F).

In a preferred embodiment, the copolymerization is carried out in the presence of at least one polymeric additive G), where the additive G) is added to the polymerization medium in completely or partially dissolved form prior to the actual copolymerization. The use of two or more additives G) is likewise in accordance with the invention. Crosslinked additives G) can likewise be used. The additives G) or mixtures thereof must merely be completely or partially soluble in the chosen polymerization medium. During the actual polymerization step, the additive G) has a number of functions. On the one hand, in the actual polymerization step, it prevents the formation of overcrosslinked polymer proportions in the copolymer which forms and, on the other hand, the additive G) is attacked randomly by active free radicals according to the generally known mechanism of graft copolymerization. This means that, depending on the additive G), greater or lesser proportions thereof are incorporated into the copolymers. In addition, suitable additives G) have the property of changing the solubility parameters of the copolymers which form during the free-radical polymerization reaction in such a way that the average molecular weights are shifted to higher values. Compared with analogous copolymers which have been prepared without the addition of the additives G), those which have been prepared with the addition of additives G) advantageously exhibit a significantly higher viscosity in aqueous solution.

Preferred additives G) are homo- and copolymers soluble in water and/or alcohols, preferably in t-butanol. Here, copolymers are also understood as meaning those with more than two different types of monomer.

Particularly preferred additives G) are homo- and copolymers of N-vinylformamide, N-vinylacetamide, N-vinylpyrrolidone, ethylene oxide, propylene oxide, acryloyldimethyltauric acid, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy) ethyl]trimethylammonium chloride (MAPTAC); polyalkylene glycols and/or alkyl polyglycols.

Particularly preferred additives G) are polyvinylpyrrolidones (e.g. Luviskol K15®, K20® and K30® from BASF), poly(N-vinylformamides), poly(N-vinylcaprolactams) and copolymers of N-vinylpyrrolidone, N-vinylformamide and/or acrylic acid, which may also be partially or completely saponified.

The molecular weight of the additives G) is preferably $10^2$ to $10^7$ g/mol, particularly preferably $0.5*10^4$ to $10^6$ g/mol.

The amount of polymeric additive G) used is, based on the total mass of the monomers to be polymerized in the copolymerization, preferably 0.1 to 90% by weight, particularly preferably 1 to 20% by weight and especially preferably 1.5 to 10% by weight.

In a further preferred embodiment, the copolymers according to the invention are crosslinked, i.e. they contain comonomers with at least two vinyl groups capable of polymerization.

Preferred crosslinkers are methylenebisacrylamide; methylenebismethacrylamide; esters of unsaturated mono- and polycarboxylic acids with polyols, preferably diacrylates and triacrylates or -methacrylates, particularly preferably butanediol and ethylene glycol diacrylate or methacrylate, trimethylolpropane triacrylate (TMPTA) and trimethylolpropane trimethacrylate (TMPTMA); allyl compounds, preferably allyl (meth)acrylate, triallyl cyanurate, maleic diallyl ester, polyallyl ester, tetraallyloxyethane, triallylamine, tetraallylethylenediamine; allyl esters of phosphoric acid; and/or vinylphosphonic acid derivatives.

A particularly preferred crosslinker is trimethylolpropane triacrylate (TMPTA). The proportion by weight of crosslinking comonomers, based on the total mass of the copolymers, is preferably up to 20% by weight, particularly preferably 0.05 to 10% by weight and especially preferably 0.1 to 7% by weight.

The polymerization medium which can be used is any organic or inorganic solvent which behaves largely inertly with regard to free-radical polymerization reactions and advantageously permits the formation of moderate or high molecular weights. Preference is given to using water; lower alcohols; preferably methanol, ethanol, propanols, iso-, sec- and t-butanol, particularly preferably t-butanol; hydrocarbons having 1 to 30 carbon atoms and mixtures of the above-mentioned compounds.

The polymerization reaction preferably takes place in the temperature range between 0 and 150° C., particularly preferably between 10 and 100° C., either at atmospheric pressure or else under increased or reduced pressure. Optionally, the polymerization can also be carried out under a protective gas atmosphere, preferably under nitrogen.

The polymerization can be triggered using high-energy electromagnetic rays, mechanical energy or the customary chemical polymerization initiators, such as organic peroxides, e.g. benzoyl peroxide, tert-butyl hydroperoxide, methyl ethyl ketone peroxide, cumene hydroperoxide, dilauroyl peroxide or azo initiators, such as, for example, azodiisobutyronitrile (AIBN).

Likewise suitable are inorganic peroxy compounds, such as, for example, $(NH_4)_2S_2O_8$, $K_2S_2O_8$ or $H_2O_2$, optionally in combination with reducing agents (e.g. sodium hydrogensulfite, ascorbic acid, iron(II) sulfate etc.) or redox systems which comprise an aliphatic or aromatic sulfonic acid (e.g. benzenesulfonic acid, toluenesulfonic acid etc.) as reducing component.

The polymerization medium which can be used is any solvent which is largely inert with regard to free-radical polymerization reactions and permits the formation of high molecular weights. Preference is given to using water and lower, tertiary alcohols or hydrocarbons having 3 to 30 carbon atoms. In a particularly preferred embodiment, t-butanol is used as reaction medium. Mixtures of two or more representatives of the potential solvents described are of course likewise in accordance with the invention. This also includes emulsions of immiscible solvents (e.g. water/hydrocarbons). In principle, all types of reaction procedure are suitable which lead to the polymer structures according to the invention (solution polymerization, emulsion processes, precipitation processes, high-pressure processes, suspension processes, bulk polymerization, gel polymerization etc.).

Preference is given to precipitation polymerization, and particular preference is given to precipitation polymerization in tert-butanol.

The list below gives 67 copolymers which are particularly suitable for the formulation of the compositions according to the invention. The various copolymers No. 1 to No. 67 are obtainable in accordance with the following preparation processes 1, 2, 3 and 4.

Process 1:

These polymers can be prepared by the precipitation process in tert-butanol. In this process, the monomers were initially introduced into 2-butanol, the reaction mixture was rendered inert and then the reaction was started after initial heating to 60° C. by adding the appropriate initiator soluble in t-butanol (preferably dilauroyl peroxide). When the reaction was complete (2 hours), the polymers were isolated by removing the solvent with suction and by subsequent vacuum drying.

Process 2:

These polymers can be prepared by the gel polymerization process in water. In this process, the monomers were dissolved in water, the reaction mixture was rendered inert and the reaction was started after initial heating to 65° C. by adding suitable initiator(s) systems (preferably $Na_2S_2O_8$). The polymer gels were then comminuted and, after drying, the polymers were isolated.

Process 3:

These polymers can be prepared by the emulsion process in water. In this process, the monomers were emulsified in a mixture of water/organic solvent (preferably cyclohexane) using an emulsifier, the reaction mixture was rendered inert using $N_2$ and then the reaction was started after initial heating to 80° C. by adding suitable initiator(s) systems (preferably $Na_2S_2O_8$). The polymer emulsions were then evaporated (cyclohexane functions as entrainer for water), thereby isolating the polymers.

Process 4:

These polymers can be prepared by the solution process in organic solvents (preferably toluene, e.g. also tert-alcohols). In this process, the monomers were initially introduced into the solvent, the reaction mixture was rendered inert and then the reaction was started after initial heating to 70° C. adding suitable initiator(s) systems (preferably dilauroyl peroxide).

The polymers were isolated by evaporating off the solvent and by subsequent vacuum drying.

Polymers with Hydrophobic Side Chains, Uncrosslinked

| No. | Composition | Preparation process |
| --- | --- | --- |
| 1 | 95 g AMPS 5 g Genapol T-080 methacrylate | 1 |
| 2 | 90 g AMPS 10 g Genapol T-080 methacrylate | 1 |
| 3 | 85 g AMPS 15 g Genapol T-080 methacrylate | 1 |
| 4 | 80 g AMPS 20 g Genapol T-080 methacrylate | 1 |
| 5 | 70 g AMPS 30 g Genapol T-080 methacrylate | 1 |
| 6 | 50 g AMPS 50 g Genapol T-080 methacrylate | 3 |
| 7 | 40 g AMPS 60 g Genapol T-080 methacrylate | 3 |
| 8 | 30 g AMPS 70 g Genapol T-080 methacrylate | 3 |
| 9 | 20 g AMPS 80 g Genapol T-080 methacrylate | 3 |
| 10 | 60 g AMPS 60 g BB10 acrylate | 4 |
| 11 | 80 g AMPS 20 g BB10 acrylate | 4 |
| 12 | 90 g AMPS 10 g BB10 methacrylate | 3 |
| 13 | 80 g AMPS 20 g BB10 methacrylate | 1 |
| 14 | 80 g AMPS 20 g Genapol LA040 acrylate | 1 |

Polymers with Hydrophobic Side Chains, Crosslinked

| No. | Composition | Preparation process |
| --- | --- | --- |
| 15 | 80 g AMPS 20 g Genapol LA040 methacrylate 0.6 g AMA | 1 |
| 16 | 80 g AMPS 20 g Genapol LA040 methacrylate 0.8 g AMA | 1 |
| 17 | 80 g AMPS 20 g Genapol LA040 methacrylate 1.0 g AMA | 1 |
| 18 | 628.73 g AMPS 120.45 g Genapol T-250 acrylate 6.5 g TMPTA | 2 |
| 19 | 60 g AMPS 40 g BB10 acrylate 1.9 g TMPTA | 4 |
| 20 | 80 g AMPS 20 g BB10 acrylate 1.4 g TMPTA | 4 |
| 21 | 90 g AMPS 10 g BB10 methacrylate 1.9 g TMPTA | 4 |
| 22 | 80 g AMPS 20 g BB25 methacrylate 1.9 g TMPTA | 1 |
| 23 | 60 g AMPS 40 g BB10 acrylate 1.4 g TMPTA | 4 |

Polymers with Hydrophobic Side Chains, Crosslinked, Grafted

| No. | Composition | Preparation process |
| --- | --- | --- |
| 24 | 95 g AMPS 5 g BB10 acrylate, 1.9 g TMPTA, 1 g Poly-NVP | 1 |
| 25 | 90 g AMPS 10 g BB10 acrylate, 1.9 g TMPTA, 1 g Poly-NVP | 1 |
| 26 | 85 g AMPS 15 g BB10 acrylate, 1.9 g TMPTA, 1 g Poly-NVP | 1 |
| 27 | 90 g AMPS 10 g BB10 methacrylate, 1.9 g TMPTA, 1 g Poly-NVP | 1 |

Polymers with Silicon-Containing Groups, Uncrosslinked

| No. | Composition | Preparation process |
| --- | --- | --- |
| 28 | 80 g AMPS, 20 g Silvet 867 | 1 |
| 29 | 80 g AMPS, 50 g Silvet 867 | 4 |

Polymers with Silicon-Containing Groups, Crosslinked

| No. | Composition | Preparation process |
| --- | --- | --- |
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers with Hydrophobic Side Chains and Cationic Groups, Uncrosslinked

| No. | Composition | Preparation process |
| --- | --- | --- |
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers with Hydrophobic Side Chains and Cationic Groups, Crosslinked

| No. | Composition | Preparation process |
| --- | --- | --- |
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers with Fluorine-Containing Groups

| No. | Composition | Preparation process |
| --- | --- | --- |
| 49 | 94 g AMPS, 2.02 g Fluowet AC 600 | 1 |
| 50 | 80 g AMPS, 20 g perfluorooctyl polyethylene glycol methacrylate, 1 g Span 80 | 3 |

Polymers with Fluorine-Containing Groups, Grafted

| No. | Composition | Preparation process |
| --- | --- | --- |
| 51 | 80 g AMPS, 10 g Fluowet AC 600, 5 g Poly-NVP | 1 |
| 52 | 70 g AMPS, 8 g perfluorooctyl ethyloxyglycerol methacrylate, 5 g Poly-NVP | 4 |

Multifunctional Polymers

| No. | Composition | Preparation process |
|---|---|---|
| 53 | 80 g AMPS, 10 g Genapol LA070, 10 g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150-methacrylate, 10 g DADMAC, 1.8 g TMPTA, 8 g Poly-N-vinylformamide | 2 |
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloxypropyldimethicone, 10 g perfluorooctyl polyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexyl polyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinyl-pyrrolidone, 20 g Silvet 7608, 10 g methacryloxy-propyldimethicone, 10 g Fluowet AC 812 | 3 |
| 62 | 60 g AMPS, 10 g DADMAC, 10 g Quat, 10 g Genapol-LA-250 crotonate, 10 g methacryloxy-propyldimethicone, 7 g Poly[acrylic acid-co-N-vinylformamide] | 1 |
| 63 | 50 g AMPS, 45 g Silvet 7608, 1.8 g TMPTA, 8 g Poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical Name of the Reactants:

| | |
|---|---|
| AMPS | acryloyldimethyltaurate, Na or $NH_4$ salt as desired |
| Genapol ® T-080 | $C_{16}$-$C_{18}$-fatty alcohol polyglycol ether with 8 EO units |
| Genapol ® T-110 | $C_{12}$-$C_{14}$-fatty alcohol polyglycol ether with 11 EO units |
| Genapol ® T-250 | $C_{16}$-$C_{18}$-fatty alcohol polyglycol ether with 25 EO units |
| Genapol ® LA-040 | $C_{12}$-$C_{14}$-fatty alcohol polyglycol ether with 4 EO units |
| Genapol ® LA-070 | $C_{12}$-$C_{14}$-fatty alcohol polyglycol ether with 7 EO units |
| Genapol ® O-150 methacrylate | $C_{16}$-$C_{18}$-fatty alcohol polyglycol ether methacrylate with 15 EO units, |
| Genapol ® LA-250 crotonate | $C_{12}$-$C_{14}$-fatty alcohol polyglycol ether crotonate with 25 EO units |
| Genapol ® T-250 methacrylate | $C_{16}$-$C_{18}$-fatty alcohol polyglycol ether methacrylate with 25 EO units |
| Genapol ® T-250 acrylate | $C_{16}$-$C_{18}$-fatty alcohol polyglycol ether methacrylate with 25 EO units |
| BB10 ® | polyoxyethylene(10) behenyl ether |
| TMPTA | trimethylolpropane triacrylate |
| Poly-NVP | Poly-N-vinylpyrrolidone |
| Silvet ® 867 | Siloxanepolyalkylene oxide copolymer |
| MBA | Methylenebisacrylamide |
| AMA | Allyl methacrylate |
| ® Y-12867 | Siloxanepolyalkylene oxide copolymer |
| Silvet ® 7608 | Polyalkylene oxide-modified heptamethyltrisiloxane |
| Silvet ® 7280 | Polyalkylene oxide-modified heptamethyltrisiloxane |
| DADMAC | Diallyldimethylammonium chloride |
| HEMA | 2-Hydroxyethyl methacrylate |
| Quat | 2-(Methacryloyloxy)ethyltrimethylammonium chloride |
| Fluowet ® AC 600 | Perfluoroalkyl ethyl acrylate |
| Span ® 80 | Sorbitan ester |

The described optional grafting of the copolymers with other polymers leads to products with particular polymer morphology which, in aqueous systems, gives optically clear gels. A potential disadvantage of the copolymers without grafting is greater or lesser opalescence in aqueous solution. This is caused by overcrosslinked polymer proportions which have hitherto been unavoidable which arise during the synthesis and are only in inadequately swollen form in water. As a result, light-scattering particles form, the size of which is significantly greater than the wavelength of visible light and are therefore the cause of the opalescence. The described, optional grafting process significantly reduces or entirely avoids the formation of overcrosslinked polymer proportions compared with conventional techniques.

The described optional incorporation both of cationic charges and also of silicon, fluorine or phosphorus atoms into the copolymers leads to products which, in cosmetic formulations, have particular sensory and rheological properties. An improvement in the sensory and rheological properties may be desired in particular for use in rinse-off products (in particular hair-treatment compositions) and also leave-on products (in particular O/W emulsions).

As well as comprising the copolymer, the dispersion concentrates according to the invention also comprise one or more emulsifiers and/or an oil phase in the stated amount. If emulsifiers are used as the sole component II, the proportion of the oil phase is thus 0% and, accordingly, the proportion of the emulsifiers is 0%, if the component II consists only of an oil phase. Preference is given to using a mixture of emulsifier and oil phase as second component.

Suitable emulsifiers are addition products of from 0 to 30 mol of alkylene oxide, in particular ethylene oxide, propylene oxide, butylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally their ethylene oxide addition products; addition products of from 15 to 60 mol of ethylene oxide onto castor oil and/or hydrogenated castor oil; polyol and, in particular, polyglycerol esters, such as, for example, polyglycerol polyricinoleate and polyglycerol poly-12-hydroxystearate. Preference is given to liquid fatty acid esters which may either be ethoxylated (PEG-10 polyglyceryl-2laurate) or as nonethoxylated (polyglyceryl-2 sesquiisostearate).

Further dispersion concentrates according to the invention preferably comprise sorbitol ester prepared by reacting sorbitol with fatty acid methyl esters or fatty acid triglycerides according to the process described in DE 197 27 950. The fatty acid radical in the fatty acid methyl esters and fatty acid triglycerides generally comprises 8 to 22 carbon atoms and can be straight-chain or branched, saturated or unsaturated. Examples thereof are palmitic acid, stearic acid, lauric acid, linoleic acid, linolenic acid, isostearic acid or oleic acid.

Suitable fatty acid triglycerides are all natural animal or vegetable oils, fats and waxes, for example olive oil, rapeseed oil, palm kernel oil, sunflower oil, coconut oil, linseed oil, castor oil, soybean oil, optionally also in refined or hydrogenated form. Since these natural fats, oils and waxes are normally mixtures of fatty acids of varying chain length, this also applies to the fatty acid radicals in the sorbitol esters used according to the invention. The sorbitol esters used according to the invention can also be alkoxylated, preferably ethoxylated.

In addition, it is possible to use anionic emulsifiers, such as ethoxylated and nonethoxylated mono-, di- or triphosphoric esters, but also cationic emulsifiers, such as mono-, di- and trialkyl quats and their polymeric derivatives.

Likewise suitable are mixtures of compounds of two or more of these classes of substance.

As well as comprising AMPS copolymer, the dispersions according to the invention can comprise one or more oils, preferably from the group of hydrocarbons, ester oils, vegetable oils and silicone oils.

The oils used according to the invention include hydrocarbon oils with linear or branched, saturated or unsaturated C7-C40-carbon chains, for example Vaseline, dodecane, isododecane, cholesterol, lanolin, hydrogenated polyisobutylenes, docosanes, hexadecane, isohexadecane, paraffins and isoparaffins;

oils of vegetable origin, in particular liquid triglycerides, such as sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's smock oil, castor oil, olive oil, groundnut oil, rapeseed oil and coconut oil; oils of animal origin, for example beef tallow, pig fat, goose grease, perhydrosqualene, lanolin; synthetic oils, such as purcellin oil, linear and/or branched fatty alcohols and fatty acid esters, preferably Guerbet alcohols having 6 to 18, preferably 8 to 10, carbon atoms; esters of linear ($C_6$-$C_{13}$)-fatty acids with linear ($C_6$-$C_{20}$)-fatty alcohols; esters of branched ($C_6$-$C_{13}$)-carboxylic acids with linear ($C_6$-$C_{20}$)-fatty alcohols, esters of linear ($C_6$-$C_{18}$)-fatty acids with branched alcohols, in particular 2-ethylhexanol; esters of linear and/or branched fatty acids with polyhydric alcohols (such as, for example, dimerdiol or trimerdiol) and/or Guerbet alcohols; alcohol esters of $C_1$-$C_{10}$-carboxylic acids or $C_2$-$C_{30}$-dicarboxylic acids, $C_1$-$C_{30}$-carboxylic monoesters and polyesters of sugar, $C_1$-$C_{30}$-monoesters and polyesters of glycerol;

waxes, such as beeswax, paraffin wax or microcrystalline waxes, optionally in combination with hydrophilic waxes, such as, for example, cetylstearyl alcohol; fluorinated and perfluorinated oils.

Monoglycerides of $C_1$-$C_{30}$-carboxylic acids, diglycerides of $C_1$-$C_{30}$-carboxylic acids, triglycerides of $C_1$-$C_{30}$-carboxylic acids, for example triglycerides of caprylic/capric acids, ethylene glycol monoesters of $C_1$-$C_{30}$-carboxylic acids, ethylene glycol diesters of $C_1$-$C_{30}$-carboxylic acids, propylene glycol monoesters of $C_1$-$C_{30}$-carboxylic acids, propylene glycol diesters of $C_1$-$C_{30}$-carboxylic acids, and propoxylated and ethoxylated derivatives of the abovementioned classes of compound.

Suitable silicone oils are dimethylpolysiloxanes, cyclomethicones, polydialkylsiloxanes $R_3SiO(R_2SiO)_xSiR_3$, where R is a methyl and ethyl, particularly preferably methyl, and x is a number from 2 to 500, for example dimethicones available under the tradenames VICASIL (General Electric Company), DOW CORNING 200, DOW CORNING 225, DOW CORNING 200 (Dow Corning Corporation). Trimethylsiloxysilicates $[(CH_2)_3SiO)_{1/2}]_x[SiO_2]y$, where x is a number from 1 to 500 and y is a number from 1 to 500. Dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example polymethylphenylsiloxanes obtainable under the tradenames SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty acid-, alcohol-, polyether-, epoxy-, fluorine- and/or alkyl-modified silicone compounds, and also polyethersiloxane copolymers, as described in U.S. Pat. No. 5,104,645 and the specifications cited therein, which may either be in liquid form or in resin form at room temperature.

The dispersion concentrates according to the invention can be prepared in various ways, an inverse emulsion polymerization or an inverse mini-emulsion polymerization being as preferred as a physical mixing of AMPS copolymer with oil/emulsifier phase and optionally water phase. The physical mixing is preferably carried out by mixing oil phase and emulsifier(s) at 10 to 60° C., preferably at room temperature, then adding AMPS copolymer(s) to about 40% by weight of the oil/emulsifier phase over a period of from 10 to 60 min, preferably about 30 min, with vigorous stirring. During this, a homogeneous paste forms. If necessary, a small amount of water can be added to improve processing. Then, the remaining oil/emulsifier phase is added with stirring and the mixture is stirred to homogeneity for a number of hours. A liquid, pourable dispersion is formed.

The dispersion concentrates according to the invention are suitable as thickener, bodying agent, emulsifier, solubilizer, dispersant, lubricant, adhesive, conditioner and/or stabilizer—in an excellent manner for the formulation of cosmetic, pharmaceutical and dermatological compositions, in particular of oil-in-water emulsions in the form of creams, lotions, cleansing milk, cream gels, spray emulsions, e.g. body lotions, aftersun lotions, sunscreen compositions and deodorant sprays.

The dispersion concentrates according to the invention are used in the cosmetic and pharmaceutical preparations in amounts by weight such that polymer concentrations are from 0.01 to 10% by weight, preferably 0.1 to 5% by weight, particularly preferably 0.5 to 3% by weight, based on the finished compositions, result.

The compositions according to the invention can comprise anionic, cationic, nonionic, zwitterionic and/or amphoteric surfactants, and also further auxiliaries and additives, cationic polymers, film formers, superfatting agents, stabilizers, biogenic active ingredients, glycerol, preservatives, pearlizing agents, dyes and fragrances, solvents, opacifiers, and also protein derivatives, such as gelatin, collagen hydrolysates, natural and synthetic-based polypeptides, egg yolk, lecithin, lanolin and lanolin derivatives, fatty alcohols, silicones, deodorizing agents, substances with keratolytic and keratoplastic action, enzymes and carrier subtances. Furthermore, antimicrobially effective agents can be added to the compositions according to the invention.

In addition, the compositions according to the invention can comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols with a relative molecular mass below 2000. In particular, the use of polyethylene glycol with a relative molecular mass between 200 and 600 and in amounts up to 45% by weight and of polyethylene glycol with a relative molecular mass between 400 and 600 in amounts of from 5 to 25% by weight is preferred. Further suitable solvents are, for example, triacetin (glycerol triacetate) and 1-methoxy-2-propanol. Short-chain anionic surfactants, in particular arylsulfonates, for example cumene- or toluenesulfonate, have a hydrotropic effect.

The examples below serve to illustrate the subject matter of the invention in more detail without limiting it thereto (the percentages are percentages by weight).

Various base formulations with a high emulsifier concentration (A1 to A6) and with a low emulsifier concentration (B1 to B6) were prepared. In this connection, different polymers were used in each case:

Polymer No. 1, 2, 4, 17, 18, 22, 27, 28, 32, 41, 44 and 46 in accordance with the above tables. The resulting polymer dispersions were assessed in terms of appearance, viscosity and stability (sedimentation upon storage at 25° C. for 3 weeks).

| 1. High emulsifier conc. | | | | | | |
|---|---|---|---|---|---|---|
| | Polymer No. | | | | | |
| | 18 A1 | 22 A2 | 17 A3 | 41 A4 | 22 A5 | 22 A6 |
| Polymer | 36.0% | 36.0% | 36.0% | 36.0% | 36.0% | 36% |
| Hostacerin DGI | 25.6% | 12.8% | 51.2% | 25.6% | 28.8% | 30% |
| Hostaphat KL 340 D | 6.4% | 19.2% | 12.8% | 38.4% | 19.2% | 18% |
| Myritol 318 | 32.0% | 32.0% | 0.0% | 16.0% | 24.0% | 16% |
| Paraffin | 0.0% | 0.0% | 0.0% | 0.0% | 0.0% | 0.0% |
| IPP | 0.0% | 0.0% | 0.0% | 0.0% | 0.0% | 0.0% |

| 1. Low emuisifier conc. | | | | | | |
|---|---|---|---|---|---|---|
| | Polymer Nr. | | | | | |
| | 1 B1 | 4 B2 | 44 B3 | 18 B4 | 22 B5 | 22 B6 |
| Polymer | 36.0% | 36.0% | 36.0% | 36.0% | 36.0% | 36% |
| Hostacerin DGI | 4.0% | 2.0% | 4.0% | 2.0% | 3.0% | 3% |
| Hostaphat KL 340 D | 1.0% | 3.0% | 1.0% | 3.0% | 2.0% | 2% |
| Myritol 318 | 59.0% | 59.0% | 0.0% | 0.0% | 29.5% | 0.0% |
| Paraffin | 0.0% | 0.0% | 59.0% | 59.0% | 29.5% | 29.5% |
| IPP | 0.0% | 0.0% | 0.0% | 0.0% | 0.0% | 29.5% |

A Mix 2-6 and initially introduce a third of the solution.
B Add the HMP polymer over the course of half an hour with stirring at 400 rpm.
C After-stir for half an hour, then add the remaining solution of A.
D After-stir for a further 5 hours.

Chemical Name of the Commercial Products Used:

| | |
|---|---|
| Hostacerin DGI | Polyglyceryl-2 sesquiisostearate |
| Myritol 318 | Caprylic/Capric triglyceride |
| IPP | Isopropyl palmitate |
| Hostaphat KL340D | Trilaureth-4 phosphate |

The invention claimed is:

1. A liquid cosmetic or pharmaceutical dispersion concentrate consisting essentially of:
   I) 20 to 80% by weight of a copolymer obtainable by free-radical copolymerization of components:
      A) acryloyldimethyltauric acid or an acryloyldimethyltaurate or a mixture thereof,
      B) optionally one or more further olefinically unsaturated, non-cationic, optionally crosslinking comonomers which have at least one oxygen, nitrogen, sulfur or phosphorus atom and have a molecular weight of less than 500 g/mol,
      C) optionally one or more olefinically unsaturated, cationic comonomers which have at least one oxygen, nitrogen, sulfur or phosphorus atom and have a molecular weight of less than 500 g/mol,
      D) optionally one or more at least monofunctional silicon-containing component(s) capable of free-radical polymerization,
      E) optionally one or more at least monofunctional fluorine-containing component(s) capable of free-radical polymerization,
      F) optionally one or more acrylically or methacrylically monofunctionalized alkyl ethoxylates according to the formula (IV)

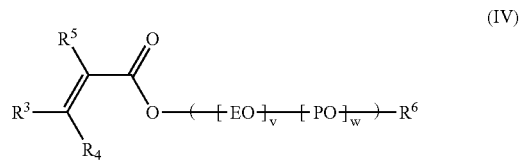

$R_3$, $R_4$, $R_5$ and $R_6$ are, independently of one another, hydrogen or n-aliphatic, isoaliphatic, olefinic, cycloaliphatic, arylaliphatic or aromatic ($C_1$-$C_{30}$)-hydrocarbon radicals,
   wherein v and w are, independently of one another, 0 to 500, where the sum of v and w must on average be $\geq 1$,
   where the distribution of the EO and PO units over the macromonomer chain may be random, block-like, alternating or gradient-like, and
   with the proviso that the component A) Is copolymerized with at least one component chosen from one of components D), to F),
   II) 20 to 80% by weight of one or more emulsifiers or an oil phase or a mixture thereof and
   III) 0 to 30% by weight of water.

2. The dispersion concentrate as claimed in claim 1, wherein the copolymer comprises 20 to 99.5% by weight, based on the total mass of the copolymer, of acryloyldimethyltauric acid, or acryloyldimethyltaurate or mixtures thereof.

3. The dispersion concentrate as claimed in claim 1, which comprises 20 to 60% by weight of the copolymer.

4. The dispersion concentrate as claimed in claim 1, which comprises 30 to 40% by weight of the copolymer.

5. The dispersion concentrate as claimed in claim 1, which comprises 30 to 80% by weight of emulsifier or oil phase or mixture thereof.

6. The dispersion concentrate as claimed in claim 1, which comprises 40 to 60% by weight of emulsifier or oil phase or mixture thereof.

7. The dispersion concentrate as claimed in claim 1, which comprises 0 to 10% by weight of water.

8. The dispersion concentrate as claimed in claim 1, which comprises 0 to 5% by weight of water.

9. A cosmetic, pharmaceutical or dermatological preparation comprising liquid cosmetic or pharmaceutical dispersion concentrate as claimed in claim 1.

10. A cosmetic, pharmaceutical or dermatological preparation in the form of an oil-in-water emulsion comprising the liquid cosmetic or pharmaceutical dispersion concentrate as claimed in claim 1.

11. A method for preparing a cosmetic, pharmaceutical or dermatological preparation comprising adding to said preparation the liquid cosmetic or pharmaceutical dispersion concentrate of claim 1.

12. A composition according to claim 1 wherein $R_3$ and $R_4$ are H or —$CH_3$.

13. A composition according to claim 1 wherein $R_3$ and $R_4$ are H; $R_5$ is H or —$CH_3$; and $R_6$ is an n-aliphatic, isoaliphatic, olefinic, cycloaliphatic, arylaliphatic or aromatic ($C_1$-$C_{30}$)-hydrocarbon radical.

14. A composition according to claim 1 wherein v and w are, independently of one another, 1 to 30.

15. A process for making a dispersion concentrate, comprising the steps of copolymerizing:
  A) acryloyldimethyltaurlc acid or an acryloyldimethyitaurate or a mixture thereof,
  B) optionally one or more further olefinically unsaturated, non-cationic, optionally crosslinking comonomers which have at least one oxygen, nitrogen, sulfur or phosphorus atom and have a molecular weight of less than 500 glmol,
  C) optionally one or more olefinically unsaturated, cationic comonomers which have at least one oxygen nitrogen. sulfur or phosphorus atom and have a molecular weight of less than 500 glmol,
  D) optionally one or more at least monofunctional silicon-containing component(s) capable of free-radical polymerization,
  E) optionally one or more at least monofunctional fluorine-containing component(s) capable of free-radical polymerization,
  F) optionally one or more acrylically or methacrylically monofunctionalized alkyl ethoxylates according to the formula (IV)

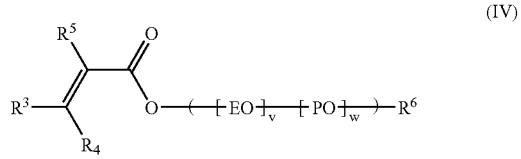

$R_3$ $R_4$, $R_6$ and $R_6$ are, independently of one another, hydrogen or n-aliphatlc, isoaliphatic, olefinic, cycloaliphatic, arylaliphatic or aromatic ($C_1$—$C_{30}$)-hydrocarbon radicals,
  wherein v and w are, independently of one another. 0 to 500, where the sum of v and w must on average be $\geq 1$, where the distribution of the EO and PO units over the macromonomer chain may be random, block-like, altemating or gradient-like.
  G) wherein the copolymerization takes place in the presence of at least one polymeric additive with number-average molecular weights of frem 200 g/mol to $10^9$ g/mol to form a copblymer,
adding the copolymer to one or more emulsiflers, an oil phase or a mixture thereof.

16. A dispersion concentrate made in accordance with claim 15.

* * * * *